United States Patent
Jerussi

(10) Patent No.: US 6,254,882 B1
(45) Date of Patent: *Jul. 3, 2001

(54) METHODS AND COMPOSITIONS FOR TREATING PULMONARY DISORDERS USING OPTICALLY PURE (S)—SALMETEROL

(75) Inventor: Thomas P. Jerussi, Framingham, MA (US)

(73) Assignee: Sepracor Inc., Marlborough, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/931,636

(22) Filed: Sep. 16, 1997

(51) Int. Cl.⁷ ............................... A61K 9/70; A61K 9/22; A61K 9/52
(52) U.S. Cl. ..................... 424/449; 424/443; 424/448; 424/451; 424/457; 424/468
(58) Field of Search ..................................... 424/464, 443, 424/448, 449, 451, 457, 468

(56) References Cited

U.S. PATENT DOCUMENTS 4,992,474   2/1991   Skidmore et al. .................. 514/653
5,380,922   1/1995   Beach et al. ........................ 562/467

FOREIGN PATENT DOCUMENTS

| 4209989A | * 11/1993 | (DE) . |
| 422889 | 4/1991 | (EP) . |
| 0556239B1 | 8/1993 | (EP) . |
| 422 889A | * 9/1993 | (EP) . |
| 2255503 | 11/1992 | (GB) . |

OTHER PUBLICATIONS

Br, J. Pharmacol. (1997), 120(5), 961–967.*
Hett et al. "Enantioselective Synthesis of Salmeterol via Asymmetric . . . " *Tetrahedron Letters 35*, 9375–9378 (1994).
Chapman et al. "Active enantiomers may cause adverse effects in asthma" *Trends Pharmacol Sci 13*, 231–232 (1992).
Boulton et al. "Enantioselective Disposition of Albuterol in Humans" *Clin. Rev. Allergy Imm. 14*, 115–138 (1996).
Nials et al. "The duration of action of non—$\beta_2$—adrenoceptor mediated . . . " *Br. J. Pharm. 120*, 961–967 (1997).

* cited by examiner

*Primary Examiner*—Shelley A. Dodson
(74) *Attorney, Agent, or Firm*—Heslin & Rothenberg, P.C.

(57) ABSTRACT

A method and composition are disclosed utilizing the pure (S) isomer of salmeterol which is a potent bronchodilator with reduced adverse effects, having a better selectivity for $\beta_2$ receptors than the corresponding R enantiomer or the racemate.

18 Claims, No Drawings

METHODS AND COMPOSITIONS FOR TREATING PULMONARY DISORDERS USING OPTICALLY PURE (S)— SALMETEROL

FIELD OF THE INVENTION

This invention relates to compositions of matter containing salmeterol. The invention also relates to methods of treating and preventing asthma, bronchitis, emphysema, and other ailments and to preventing bronchospasms in patients with obstructive airway or allergic disorders.

BACKGROUND OF THE INVENTION

Asthma, bronchitis and emphysema are known as Chronic Obstructive Pulmonary Diseases (COPD). COPD is characterized as generalized airway obstruction, particularly of small airways, associated with varying degrees of symptoms of chronic bronchitis, asthma, and emphysema. The term COPD was introduced because these conditions often coexist, and it may be difficult in an individual case to decide which is the major condition producing the obstruction. Airway obstruction is defined as an increased resistance to airflow during forced expiration. It may result from narrowing or restriction of an airway secondary to intrinsic airway disease, from excessive collapse of the airway during a forced expiration secondary to pulmonary emphysema, from bronchospasm as in asthma, or may be due to a combination of these factors. Although obstruction of large airways may occur in all these disorders, particularly in asthma, patients with severe COPD characteristically have major abnormalities in their small airways, namely those less than 2 mm internal diameter, and much of the obstruction of their airway is situated in this zone. The airway obstruction is irreversible except for that which can be ascribed to asthma.

Asthma is a reversible obstructive respiratory disorder characterized by increased responsiveness of the airway. Asthma can occur secondarily to a variety of stimuli. The underlying mechanisms are unknown, but inherited or acquired imbalance of adrenergic and cholinergic control of airway diameter has been implicated. Asthmatics manifesting such imbalance have hyperactive bronchi and, even without symptoms, bronchoconstriction may be present. Overt asthma attacks may occur when such individuals are subjected to various stresses, such as viral respiratory infection, exercise, emotional upset, nonspecific factors (e.g., changes in barometric pressure or temperature), inhalation of cold air or irritants (e.g., gasoline fumes, fresh paint and noxious odors, or cigarette smoke), exposure to specific allergens, and ingestion of aspirin or sulfites in sensitive individuals. Those whose asthma is precipitated by allergens (most commonly airborne pollens and molds, house dust, animal danders) and whose symptoms are IgE-mediated are said to have allergic or "extrinsic" asthma. They account for about 10 to 20% of adult asthmatics; in another 30 to 50%, symptomatic episodes seem to be triggered by non-allergenic factors (e.g., infection, irritants, emotional factors), and these patients are said to have nonallergic or "intrinsic" asthma. In many persons, both allergenic and non-allergenic factors are significant.

Racemic salmeterol is a $\beta_2$ adrenoceptor-selective sympathomimetic, whose primary use is as a long-acting bronchodilator for the prevention of bronchospasm in patients with obstructive airway disease such as asthma, bronchitis and emphysema.

Most of the $\beta_2$ agonists cause somewhat similar adverse effects. These adverse effects include but are not limited to cardiovascular effects such as palpitations, increased heart rate, and tachycardia; central nervous system symptoms such as nervousness, dizziness, headache and drowsiness; respiratory side effects such as dyspnea, wheezing, drying or irritation of the oropharynx, coughing, chest pain and chest discomfort; hand tremors, muscle tremors, and immediate hypersensitivity reactions such as urticaria, angioedema, rash and even bronchospasms.

Furthermore, patients have a tendency to develop a tolerance to the bronchodilating effect of $\beta_2$ agonists. This is related to desensitization, which is one of the most clinically significant phenomena involving the β-adrenergic receptor. It has been observed that patients in prolonged β-agonist therapy have a tendency to increase the dosage of drug they use. This occurs because after prolonged administration, the β receptor appears to become desensitized to the agonist, thus requiring larger doses of the compound to effect an equivalent physiological response.

The problem of desensitization is especially significant in the treatment of diseases involving bronchospasms, such as asthma. The treatment of asthma usually involves the self-administration either orally or by aerosol, of β-adrenergic agonists such as the racemic mixture of salmeterol. Asthmatic patients utilizing β-agonists for a prolonged time gradually increase the self-administered dose in order to get a sufficient amount of bronchodilation and relief in breathing. As a result of this increased dosage, the agonist acts on the β receptors of the heart and vasculature to cause cardiovascular stress and other adverse effects.

A general suggestion has been made in the literature that the (R) enantiomer is the $\beta_2$ stimulatory enantiomer (eutomer) of most, if not all, phenethanolamine $\beta_2$ adrenoceptor-selective sympathomimetics, and this general teaching has been applied to salmeterol. Thus U.S. Pat. No. 4,992,474 states that the compounds of the genus that includes salmeterol exist in enantiomeric forms and that compounds in which the alcohol carbon is in the R configuration are preferred. Similarly, Chapman et al. [*Trends Pharmacol Sci* 13, 231–232 (1992)] discussed the problem of chirality in $\beta_2$ adrenoceptor-selective sympathomimetics, and concluded that agonist activity resides in the R enantiomer of isoprenaline, salbutamol, salmeterol and terbutaline. British Patent 2,255,503 discloses the use of a single enantiomer of various $\beta_2$ adrenoceptor-selective sympathomimetics, including salmeterol, and indicates that, in the case of salmeterol the enantiomer to use to minimize side effects is the (R) enantiomer. As recently as 1996, those of skill in the art have continued to suggest that "The β adrenoceptor activity of albuterol and other agonists [salmeterol is among those named] has been shown to reside mainly in the R-enantiomer (eutomer) with little or no adrenoceptor stimulation attributed to the S-enantiomer (distomer)." [Boulton and Fawcett *Clin. Rev. Allergy Immunol.* 14, 115–138 (1996)] Thus the present invention—the use of the S enantiomer—goes directly against the clear teachings of all of the known art.

SUMMARY OF THE INVENTION

It has now been discovered that the S enantiomer of salmeterol is an effective bronchodilator whose administration does not precipitate certain adverse effects associated with the administration of the racemic mixture or (R)-salmeterol.

In one aspect the invention relates to methods of inducing bronchodilation and preventing bronchoconstriction with salmeterol, comprising administering to an individual a quantity of optically pure S isomer sufficient to induce bronchodilation or prevent bronchoconstriction. Preferably the salmeterol comprises at least 90% by weight of the S isomer and not more than 10% by weight of the R isomer; more preferably the salmeterol comprises at least 99% by weight of the S isomer and 1% or less by weight of the R isomer. The (S)-salmeterol may be administered by subcutaneous injection, intravenous infusion, inhalation, transdermal delivery or oral administration. Inhalation is preferred. The amount administered by inhalation is about 200 µg to about 2 mg per day, which is optimally divided into at least two doses, each in an amount of about 100 µg to about 1 mg per unit dosage. The method elicits a bronchodilator effect while avoiding the concomitant liability of side effects associated with $\beta_1$ adrenergic receptor activation by administering an amount of (S)-salmeterol, or a pharmaceutically acceptable salt thereof, sufficient to prevent bronchospasms but insufficient to cause the side effects.

In another aspect the invention relates to bronchodilator compositions in the form of oral unit dosage forms or formulations suitable for administration by inhalation, e.g. solution or suspension in a suitable propellant for use in a metered-dose inhaler or sterile aqueous solution for nebulization. The compositions comprise a pharmaceutically acceptable propellant (for aerosols) or carrier (for inhalation solutions, tablets and capsules) and (S)-salmeterol, or a pharmaceutically acceptable salt thereof. As before the (S)-salmeterol should preferably contain at least 90% by weight of (S)-salmeterol and less than 10% by weight of (R)-salmeterol. A preferred bronchodilator composition is in the form of an aerosol formulation.

DETAILED DESCRIPTION OF THE INVENTION

The present invention encompasses a method of eliciting a bronchodilator effect while avoiding the concomitant liability of adverse effects, particularly those associated with $\beta_1$ adrenergic receptor stimulation. The racemic mixture of salmeterol causes bronchial smooth muscle relaxation and modulates inhibition of mediator release; however, even when the compound is administered by inhalation, the racemic mixture causes adverse effects, as described in the Physician's Desk Reference (PDR). These adverse effects include tachycardia, palpitations, urticaria, angioedema, rash, bronchospasms, headache, tremors, nervousness, and paradoxical bronchospasms. Also included in the term "adverse effects" are dizziness, fatigue, hoarseness, backaches, nausea, vomiting, drowsiness, weakness, flushed feeling, sweating, unusual taste, muscle cramps, angina, vertigo, central stimulation and insomnia.

The term "substantially free of the R stereoisomer" as used herein means that the composition contains at least about 90% by weight of (S)-salmeterol and 10% or less by weight of (R)-salmeterol. In a more preferred embodiment the composition contains at least 99% by weight (S)-salmeterol and 1% or less of (R)-salmeterol.

The term "eliciting a bronchodilator effect" means relief from the symptoms associated with obstructive airway diseases, which include but are not limited to respiratory distress, wheezing, coughing, shortness of breath, tightness or pressure in the chest and the like.

The active compound of the compositions and methods of the invention is an optical isomer of salmeterol. Racemic salmeterol is commercially available as the 1-hydroxy-2-naphthoic acid salt from Glaxo Wellcome under the trade name of Serevent®. It is supplied as an aerosol formulation for inhalation. The preparation of the racemic compound is described in U.S. Pat. Nos. 4,992,474 and 5,380,922. The preparation of the R enantiomer is also described in U.S. Pat. No. 4,992,474. Chemically, the compound of the invention is the S enantiomer of 4-hydroxy-$\alpha^1$-[[[6(4-phenylbutoxy)-hexyl]amino]methyl]-1,3-benzenedimethanol (CAS Registry No. 135271-48-6). The preparation of the individual enantiomers is described by Hett et al. in *Tetrahedron Letters* 35, 9375–9378 (1994). Salmeterol is available commercially only as the racemate, (R) plus (S) in a 1:1 ratio, and the generic name salmeterol refers to this enantiomeric mixture.

Experimental Procedures

Materials

Wildtype *Spodoptera frugiperda* (Sf 9) cells were obtained from American Type Culture Collection. Tissue culture reagents were purchased from Gibco and Sigma. The β-agonists (−) isoproterenol and (−) norepinephrine were from Sigma, [$^{125}$I] idoopindolol was from NEN Dupont, and all other reagents were of the highest grade commercially available.

Cell Culture

Sf9 cells were cultured in a spinner flask (80 rpm) at 27° C. using TNM-FH medium containing 10% fetal bovine serum and antibiotics (0.25 µg/ml Fungizone, 50 µg/ml Streptomycin, 50 µg/ml Penicillin).

Preparation of Human $\beta_1$ and $\beta_2$-Adrenergic Receptors

Recombinant baculoviruses containing the cDNA encoding the human $\beta_1$AR (adrenergic receptors) or $\beta_2$AR were used to infect Sf9 cells. Forty-eight hours post-infection the cells were harvested by centrifugation (1,000×g, 20 min), washed once with ice cold phosphate buffered saline (PBS) and then lysed in ice cold buffer A (50 mM Tris-HCl, pH 75.5, 5 mM EDTA, 20 µg/ml aprotinin, 20 µg/ml benzamidine) using a Brinkmann polytron (2×20 sec). The homogenate was centrifuged at 40,000×g for 20 min, the pellet was washed once with buffer A and then resuspended in buffer A at a concentration of ~20 pmol βAR/ml.

Competitive Binding Studies

Human $\beta_2$ARs were determined to bind the non-subtype selective β-antagonist [$^{125}$I] iodopindolol with a $K_d$ of 20 pM while $\beta_1$ARs had a Kd of 2 nM for [$^{125}$I] iodopindolol. The ability of the various compounds tested in this study ((−) isoproterenol, (−) norepinephrine, ICI118551; R-, RS- and S-albuterol; and R-, RS- and S-salmeterol) to compete with [$^{125}$I] iodopindolol binding to human $\beta_1$ARs and $\beta_2$ARs was then assessed. The incubations contained Sf9 cell membranes (22 fmol of $\beta_1$AR or $\beta_2$AR), 45–85 pM [$^{125}$I] iodopindolol and various concentrations of competing ligand ($10^{-11}$ to $10^{-3}$ M) in 25 mM Tris-HCl, pH 7.5, 2 mM MgCl$_2$, 0.5 mM ascorbic acid. The samples were incubated for 60 min at 22° C. before filtration on GF/C glass fiber filters using a 48 place Brandel cell harvester. The filters were then washed 4 times with ~5 ml of ice cold 25 mM Tris-HCl, pH 7.5, 2 mM MgCl$_2$ buffer and counted in a gamma counter.

Binding ($K_d$, nM) of β-Adrenergic Agonists

| β-Agonist | $β_1$ (nM) | $β_2$ (nM) | $β_2$ Selectivity Ratio |
|---|---|---|---|
| (−)-Isoproterenol | 20.1 | 41.7 | 0.48 |
| (RS)-Albuterol | 2,980 | 668 | 4.5 |
| (R)-Albuterol | 1,540 | 236 | 6.5 |
| (S)-Albuterol | 111,000 | 33,600 | 3.3 |
| (R,R;S,S)-Formoterol | 192 | 5.2 | 37 |
| (R,R)-Formoterol | 113 | 2.9 | 39 |
| (S,S)-Formoterol | 6,800 | 3,100 | 2.2 |
| (RS)-Salmeterol | 297 | 2.63 | 113 |
| (R)-Salmeterol | 190 | 1.65 | 115 |
| (S)-Salmeterol | 5,060 | 10.9 | 464 |

It can be seen that although (S)-salmeterol has about one-fourth to one-seventh the receptor affinity of racemic and (R)-salmeterol, respectively, at the $β_2$-site, it is 4-fold more selective (464 vs. 113 and 115). Moreover, (S)-salmeterol has greater than 20-times the receptor affinity of (R)-albuterol.

In a study in vitro, the respective relaxant and chrontrophic effects of albuterol, formoterol, and salmeterol and their enantiomers were determined for isolated guinea pig tracheal strips and right atria.

Methods and Materials

Male Hartley guinea pigs weighing roughly 300–450 g were used for these experiments. The guinea pigs were acclimatized under a 12-hr light-dark cycle for a one-week period following delivery from the supplier.

Experiments with Isolated Tracheal Strips

Prior to sacrifice, the guinea pigs were anesthetized via inhalation of carbon dioxide. Each trachea was rapidly excised and placed in ice-cold physiological salt solution, type 1 (PSS-1). The PSS-1 contained the following: 137 mM NaCl, 2. mM KCl, 1.8 mM $CaCl_2$, 0.93 mM $MgCl_2$, 0.35 mM $NaH_2PO_4$, 11.9 mM $NaHCO_2EDTA$ and 5.5 mM dextrose. Each trachea was cut longitudinally on the ventral side and the strips opened into strips which were suspended in a tissue bath containing 15 mL of PSS-1 maintained at 37° C. The PSS-1 was oxygenated with 95% $O_2$/5% $CO_2$ to maintain pH at 7.4. A resting tension of 1.0 g was placed on the strips.

After a 30-min equilibration period, the strips were contracted three times by the addition of 0.3 $\mu M$ carbachol. The strips were washed between each contraction with fresh PSS-1. Following an additional 30-min equilibration period, the strips were contracted by addition of 30 $\mu M$ histamine to the tissue bath. Once an equilibrium response was obtained, increasing concentrations of vehicle or test compound were added to the tissue baths in half-log increments until a concentration of 1000 nM was reached. Each new concentration was added to the bath after the response to the previous concentration had reached equilibrium (typically within 15–30 min). After the response to the last concentration of each test compound reached a maximum, 1 mM papaverine was added to the bath to determine the maximum relaxation possible. The response to each concentration of test compound evaluated was then normalized as a percentage of the maximum relaxant response obtained following treatment with 1 mM papaverine. (NOTE: For these experiments, inclusion of 1 mM papaverine in the tissue baths produced complete relaxation of histamine-contracted tracheal strips.)

The concentration-dependent response to each test compound was evaluated using six tracheal strips on at least two different days. The concentration-dependent response to the vehicle was evaluated using five tracheal strips on at least two different days.

Experiments with Isolated Right Atria

Prior to sacrifice, the guinea pigs were anesthetized via inhalation of carbon dioxide. The heart was then rapidly excised and placed in ice-cold physiological salt solution, type 2 (PSS-2). The PSS-2 contained the following: 117 mM NaCl, 4.3 mM KCl, 3.5 mM $CaCl_2$, 0.1 mM $K_2HPO_4$, 1.2 mM $MgCl_2$, 25 mM $NaHCO_3$, 0.6 mM $Na_2EDTA$ and 15 mM dextrose. The PSS-2 was oxygenated with 95% $O_2$/5% $CO_2$ to maintain pH at 7.4.

Right atria were suspended in a tissue bath containing 15 mL of PSS-2 maintained at 30° C. A resting tension of 0.5 g was placed on each atrium, and the rate of contraction was monitored at 5-min intervals until a stable rate was obtained (typically with 30 min). The atria were washed once with fresh PSS-2 during the equilibration period. Increasing concentrations of vehicle or test compound were then added to the tissue baths in half-log increments until a concentration of 1000 nM was reached. Each new concentration of test compound was added to the bath after the response to the previous concentration had reached equilibrium (typically within 5 min). After the response to the last concentration of each test compound reached a maximum, the adenylate cyclase stimulator forskolin was added to the bath at a final concentration of 1 $\mu M$. The response to each concentration of test compound evaluated was then normalized as a percentage of the positive chronotropic response obtained following treatment with 1 $\mu M$ forskolin. (NOTE: For these experiments, inclusion of 1 $\mu M$ forskolin in the tissue baths increased the rate of spontaneous contraction from a basal value of roughly 140–170 bpm to a value of approximately 195–250 bpm.)

The concentration-dependent response to each test compound was evaluated on six right atria. The concentration-dependent response to the vehicle was evaluated on five right atria.

For these experiments, each test substance was initially solubilized in 100% dimethylsulfoxide (DMSO) at a concentration of 1 mM. This stock solution was serially diluted using PSS-1 or PSS-2 to obtain the desired final concentrations. No clouding of the PSS was observed for any of the test compounds evaluated. At the highest concentration of test compound evaluated, i.e., 1000 nM, the concentration of DMSO in the tissues bath was <1%.

Each test substance was prepared within two to three hours of testing.

The data were analyzed by linear regression. Mean values calculated as a percentage of the maximum relaxation or atrial rate produced by 1 mM papaverine of 1 $\mu M$ forskolin, respectively, were plotted as a function of log dose and fitted with regression lines. $EC_{50}$ values—i.e. midpoint between 100% and the maximum relaxation or the minimum atrial rate for the vehicle—were then determined and tabulated below.

| β-Agonist | EC$_{50}$ (nM) Determined by Linear Regression* of Percent Maximum Response | | |
|---|---|---|---|
| | Tracheal Relaxation | Atrial Rate | Selectivity[#] Ratio |
| (RS)-Albuterol | 673 | 272 | 0.40 |
| (R)-Albuterol | 747 | 177 | 0.24 |
| (S)-Albuterol | 10$^5$ | >10$^4$ | — |
| (R,R;S,S)-Formoterol | 9.4 | 5.7 | 0.61 |
| (R,R)-Formoterol | 2.5 | 6.3 | 2.5 |
| (S,S)-Formoterol | 3,463 | >10$^4$ | >11 |
| (RS)-Salmeterol | 273 | 3,516 | 12.9 |
| (R)-Salmeterol | 149 | 1,732 | 11.6 |
| (S)-Salmeterol | 3,150 | >10$^{11}$ | >10$^7$ |

*r(log-lin) = 0.9453–0.9968
[#]selectivity ratio for tracheal relaxation

With respect to tracheal relaxation, it appears that full efficacy could be achieved for (S)-salmeterol. It was equivalent in potency (extrapolated from three data points) to (S,S)-formoterol but significantly less potent than racemic formoterol or its (R,R)-enantiomer. (R)-Albuterol showed a potency approximately four times that of (S)-salmeterol with respect to tracheal relaxation. (S)-Salmeterol had essentially the same effect on atrial rate as the vehicle control. Therefore, the selectivity ratio for tracheal relaxation was too large to determine (estimated at 10$^7$).

The selectivity of (S)-salmeterol for β$_2$-adrenergic receptors translates into fewer β$_1$-mediated side effects and a better therapeutic index.

The magnitude of a prophylactic or therapeutic dose of (S)-salmeterol in the management of disease will vary with the severity of the condition to be treated, and the route of administration. The dose, and perhaps the dose frequency, will also vary according to the age, body weight, and response of the individual patient. In general, the total daily dose ranges when administered by inhalation, for the conditions described herein, is from about 200 μg to about 2000 μg, in single or divided doses. Preferably, a daily dose range should be between about 500 μg to about 1000 μg, in single or divided doses. In managing the patient, the therapy should be initiated at a lower dose, perhaps about 200 μg to about 400 μg, and increased up to about 2×200 μg or higher depending on the patient's global response. When administered orally, the preferred dose range is from 0.1 to 1.0 mg per day. It is further recommended that children, and patients over 65 years, and those with impaired renal, or hepatic function, initially receive low doses, and that they be titrated based on individual responses) and blood level(s). It may be necessary to use dosages outside these ranges in some cases as will be apparent to those skilled in the art. Further, it is noted that the clinician or treating physician would know how and when to interrupt, adjust, or terminate therapy in conjunction with individual patient response.

The above-described dosage amounts and dose frequency schedule encompass an amount sufficient to alleviate bronchospasms but insufficient to cause adverse effects.

Any suitable route of administration may be employed for providing the patient with an effective dosage of (S)-salmeterol. For example, oral, rectal, parenteral (subcutaneous, intramuscular, intravenous), transdermal, and like forms of administration may be employed. Dosage forms include tablets, troches, dispersions, suspensions, solutions, capsules, patches, and the like.

The pharmaceutical compositions of the present invention comprise (S)-salmeterol as the active ingredient, or a pharmaceutically acceptable salt thereof, and may also contain a pharmaceutically acceptable carrier, and optionally, other therapeutic ingredients.

The term "pharmaceutically acceptable salts" or "a pharmaceutically acceptable salt thereof" refer to salts prepared from pharmaceutically acceptable non-toxic acids including inorganic acids and organic acids. Suitable pharmaceutically acceptable acid addition salts for the compound of the present invention include acetic, benzenesulfonic (besylate), benzoic, camphorsulfonic, citric, ethenesulfonic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic, and the like. The 1-hydroxy-2-naphthoic acid salt is particularly preferred.

Preferred unit dosage formulations are those containing an effective dose, as recited, or an appropriate fraction thereof, of the active ingredient. It should be understood that in addition to the ingredients particularly mentioned above, the formulations of this invention may include other agents conventional in the art having regard to the type of formulation in question. For example, formulations for oral administration may include carriers such as starches, sugars, microcrystalline cellulose, diluents, granulating agents, lubricants, binders, disintegrating agents, flavoring agents and the like. The compositions include compositions suitable for oral, rectal, parenteral (including subcutaneous, transdermal, intramuscular, and intravenous) and inhalation.

The most preferred route of the present invention is inhalation. Formulations suitable for inhalation include sterile solutions for nebulization comprising a therapeutically effective amount of S-salmeterol substantially free of its R-enantiomer, or a pharmaceutically acceptable salt thereof, dissolved in aqueous saline solution and optionally containing a preservative such as benzalkonium chloride or chlorobutanol, and aerosol formulations comprising a therapeutically effective amount of S-salmeterol substantially free of its R-enantiomer, or a pharmaceutically acceptable salt thereof, dissolved or suspended in an appropriate propellant (e.g., HFA-134a, HFA-227, or a mixture thereof, or a chlorofluocarbon propellant such as a mixture of Propellants 11, 12, and/or 114) optionally containing a surfactant. Aerosols may be conveniently presented in unit dosage form and prepared by any of the methods well-known in the art of pharmacy. The preparation of a particularly desirable aerosol formulation is described in European Patent 556239, the disclosure of which is incorporated herein by reference. Also suitable are dry powder formulations comprising a therapeutically effective amount of S-salmeterol substantially free of its R-enantiomer, or a pharmaceutically acceptable salt thereof, blended with an appropriate carrier and adapted for use in connection with a dry-powder inhaler.

The invention is further defined by reference to the following examples describing in detail the pharmacological characterization of the compound, and the preparation of compositions of the present invention. It will be apparent to those skilled in the art, that many modifications, both to materials, and methods, may be practiced without departing from the purpose and interest of this invention.

EXAMPLE 1

INHALATION

| Formula | Quantity contained in Each Metered Dose Dispenser 12.5 g Canister |
|---|---|
| (S)-salmeterol 1-hydroxy-2-naphthoate salt | 2 g |
| trichloromonofluoromethane | 5 g |
| dichlorodifluoromethane | 5 g |
| lecithin | 0.5 g |

The metered dose dispenser contains micronized (S)-salmeterol 1-hydroxy-2-naphthoate in suspension. Each actuation delivers 100 μg of (S)-salmeterol salt from the mouthpiece. Each canister provides about 200 inhalations.

EXAMPLE 2

ORAL FORMULATION
Tablets:

| Formula | Quantity per Tablet (mg.) | |
|---|---|---|
|  | A | B |
| (S)-salmeterol 1-hydroxy-2-naphthoate | 0.12 | 0.25 |
| lactose | 41.38 | 41.25 |
| cornstarch | 3.0 | 3.0 |
| water (per thousand Tablets)* | 30.0 ml | 30.0 ml |
| cornstarch | 5.00 | 5.00 |
| magnesium stearate | 0.50 | 0.50 |
|  | 50.00 | 50.00 |

*The water evaporates during manufacture

The salmeterol is blended with the lactose until a uniform blend is formed. The smaller quantity of cornstarch is blended with the water to form the resulting cornstarch paste. This is then mixed with said uniform blend until a uniform wet mass is formed. The remaining cornstarch is added to the resulting wet mass and mixed until uniform granules are obtained. The granules are then screened through a suitable milling machine, using a ¼ inch stainless steel screen. The milled granules are then dried in a suitable drying oven until the desired moisture content is obtained. The dried granules are then milled through a suitable milling machine, using ¼ mesh stainless steel screen. The magnesium stearate is then blended and the resulting mixture is compressed into tablets of desired shape, thickness, hardness and disintegration.

Soft gelatin capsules may be prepared with a mixture of salmeterol naphthoate in a digestible oil such as soybean oil, lecithin, cottonseed oil, or olive oil wherein the mixture is injected by means of a positive pressure pump into gelatin, such that each dosage unit contains 0.1 mg to 2 mg of S-salmeterol. The capsules are washed and dried.

Hard gelatin capsules may be prepared as follows:

EXAMPLE 3

ORAL FORMULATION - CAPSULES

| Formula | Quantity per capsule in mg | | |
|---|---|---|---|
|  | A | B | C |
| S-salmeterol 1-hydroxy-2-naphthoate | 5 | 25 | 50 |
| Lactose | 130 | 180 | 230 |
| Cornstarch | 60 | 60 | 65 |
| Magnesium Stearate | 5 | 5 | 5 |
| Fill Weight | 200 | 270 | 350 |

The S-salmeterol, lactose and cornstarch are blended until uniform and then the magnesium stearate is blended into the resulting powder, which is sieved and filled into suitably sized, two-piece, hard gelatin capsules using conventional machinery. Other doses may be prepared by altering the fill weight and, if necessary, changing the capsule size to suit. It is often desirable to mill or granulate the S-salmeterol naphthoate to provide a free-flowing powder for tabletting or encapsulation, when employing dry-powder techniques.

What is claimed is:

1. A method of inducing bronchodilation with salmeterol, comprising administering to a human a quantity of optically pure S isomer sufficient to induce said bronchodilation.

2. The method according to claim 1, wherein the salmeterol comprises at least 90% by weight of the S isomer and not more than 10% by weight of the R isomer.

3. The method according to claim 1, wherein the salmeterol comprises at least 99% by weight of the S isomer and 1% or less by weight of the R isomer.

4. The method of claim 1 wherein (S)-salmeterol is administered by subcutaneous injection, intravenous infusion, inhalation, transdermal delivery or oral administration.

5. A method according to claim 4, wherein the optically pure (S)-salmeterol is administered by inhalation.

6. The method according to claim 5 wherein the amount administered by inhalation is about 200 μg to about 2 mg per day.

7. The method according to claim 5 wherein the optically pure (S)-salmeterol is administered in an amount of about 100 μg to about 1 mg per unit dosage.

8. A method according to claim 1, wherein the optically pure (S)-salmeterol is administered orally.

9. A method of preventing bronchoconstriction with salmeterol, comprising administering to a human a quantity of optically pure S isomer sufficient to prevent said bronchoconstriction.

10. The method according to claim 9, wherein the salmeterol comprises at least 90% by weight of the S isomer and not more than 10% by weight of the R isomer.

11. The method according to claim 9, wherein the salmeterol comprises at least 99% by weight of the S isomer and 1% or less by weight of the R isomer.

12. The method of claim 9 wherein (S)-salmeterol is administered orally or by inhalation.

13. The method according to claim 12 wherein the amount administered by inhalation is about 200 μg to about 2 mg per day.

14. The method according to claim 13 wherein the (S)-salmeterol is administered in an amount of about 100 μg to about 1 mg per unit dosage.

15. A method for eliciting a bronchodilator effect while avoiding the concomitant liability of side effects associated with $\beta_1$ adrenergic receptor activation which comprises administering to a human in need of bronchodilation an amount of (S)-salmeterol, or a pharmaceutically acceptable salt thereof, sufficient to prevent bronchospasms but insufficient to cause said side effects, said (S)-salmeterol containing at least 90% by weight of (S)-salmeterol and less than 10% by weight of (R)-salmeterol.

16. A method for preventing bronchoconstriction while avoiding the concomitant liability of side effects associated with $\beta_1$ adrenergic receptor activation which comprises administering to a human at risk from bronchoconstriction an amount of (S)-salmeterol, or a pharmaceutically acceptable salt thereof, sufficient to prevent bronchospasms but insufficient to cause said side effects, said (S)-salmeterol containing at least 90% by weight of (S)-salmeterol and less than 10% by weight of (R)-salmeterol.

17. A pharmaceutical composition in the form of an aerosol formulation, which comprises a pharmaceutically acceptable propellant and (S)-salmeterol, or a pharmaceutically acceptable salt thereof, said (S)-salmeterol containing at least 90% by weight of (S)-salmeterol and less than 10% by weight of (R)-salmeterol.

18. An oral unit dosage form, which comprises a pharmaceutically acceptable carrier and (S)-salmeterol, or a pharmaceutically acceptable salt thereof, in the form of a tablet or capsule, said (S)-salmeterol containing at least 90% by weight of (S)-salmeterol and less than 10% by weight of (R)-salmeterol.

* * * * *